United States Patent [19]

de Montigny et al.

[11] Patent Number: 4,837,166

[45] Date of Patent: * Jun. 6, 1989

[54] ASSAYING METHOD FOR PRIMARY AMINES USING AROMATIC DIALDEHYDES

[75] Inventors: Pierre M. R. de Montigny, Fords, N.J.; Larry A. Sternson, Berwyn, Pa.; Arnold J. Repta, Lawrence, Kans.; John F. Stobaugh, Lawrence, Kans.; Takeru Higuchi, deceased, late of Lawrence, Kans., Martin B. Dickinson, Jr., co-executor; Kenji W. Higuchi, co-executor, Spokane, Wash.

[73] Assignee: Oread Laboratories, Inc., Lawrence, Kans.

[*] Notice: The portion of the term of this patent subsequent to Jul. 19, 2005 has been disclaimed.

[21] Appl. No.: 39,743

[22] Filed: Apr. 20, 1987

Related U.S. Application Data

[63] Continuation-in-part of Ser. No. 707,676, Mar. 4, 1985, abandoned.

[51] Int. Cl.$^4$ .................... G01N 21/77; G01N 27/26; G01N 33/68
[52] U.S. Cl. .................... 436/111; 204/1 T; 436/86; 436/89; 436/109; 436/150; 436/161; 436/172
[58] Field of Search .................... 436/86, 89, 90, 109, 436/111, 128, 149, 150, 161, 172; 204/1 T

[56] References Cited

U.S. PATENT DOCUMENTS

| | | | |
|---|---|---|---|
| 3,718,432 | 2/1973 | Roth | 436/90 X |
| 3,892,530 | 7/1975 | Felix et al. | 436/90 |
| 3,933,430 | 1/1976 | Hare | 436/90 |
| 4,359,323 | 11/1982 | LePage | 436/89 |
| 4,501,816 | 2/1985 | Molla | 436/34 |
| 4,670,403 | 6/1987 | Ishida et al. | 436/90 |

FOREIGN PATENT DOCUMENTS

| | | |
|---|---|---|
| 2102985 | 9/1971 | Fed. Rep. of Germany . |
| 0138092 | 4/1985 | European Pat. Off. . |
| 2534029 | 6/1984 | France . |

OTHER PUBLICATIONS

Kobayashi et al., Anal. Biochem., vol. 112, pp. 99-104, 1981.
Honda et al., J. of Chromatography, vol. 303, pp. 173-176, 1984.
Miura et al., Chemical Abstracts, vol. 96, Abstract No. 96:65120r, 1981.
Ishida et al., J. of Chromatography, vol. 204, pp. 143-148, 1981.
Gardner et al., Anal. Biochem., vol. 101, pp. 61-65, 1980.
Allison et al., Anal. Chem., vol. 56, pp. 1089-1096, 1984.
Miura et al., Anal. Biochem., vol. 139, pp. 432-437, 1984.
Chemical Abstracts, 20064F, vol. 101, (1984), Miura et al.
Reaction of o-Phthalaldehyde with Alanine and Thiols: Kinetics and Mechanism Osborne S. Wong, 1985 American Chemical Society, vol. 107, p. 6421 of J. Am. Chem. Soc.
de Montigny et al "Naphthalene-2,3-dicarboxaldehyde/Cyanaide Ion: A Rationally Designed Fluorogenic Reagent for Primary Amines," Reprinted from Analytical Chemistry, vol. 59, p. 1096, Apr. 15, 1987.
Matuszewski et al. "N-Substituted 1-Cyanobenz[f]isoindole: Evaluation of Fluorescence Efficiencies of a New Fluorogenic Label for Primary Amines and Amino Acids", Reprinted from Analytical Chemistry, vol. 59, p. 1102, Apr. 15, 1987.
Carlson et al, "New Derivatizing Agents for Amino Acids and Peptides. 1. Facile Synthesis of N-Substituted 1-Cyanobenz[f]isoindoles and Their Spectroscopic Properties", Reprinted from the Journal of Organic Chemistry, 1986, 51,3978.

Primary Examiner—Robert J. Hill, Jr.
Attorney, Agent, or Firm—Burns, Doane, Swecker & Mathis

[57] ABSTRACT

A method of assaying primary amines or cyanide is disclosed. The process is carried out by reacting a substituted or unsubstituted naphthalene-2,3-dicarboxaldehyde or o-phthalaldehyde, reactive with primary amines and cyanide, with cyanide ions and at least one primary amine to form an adduct amenable to fluorometric or electrochemical assaying techniques. The adduct is then fluorometrically or electrochemically assayed.
Also disclosed are 1-cyano-benz[f]isoindole adducts.

13 Claims, 14 Drawing Sheets

NDA-CN-ASPARTAME IN BORATE BUFFER
pH = 9.5

BENZOISOINDOLE PRODUCTS OF AMINO ACID MIXTURES

4 PICOMOLES INJECTION 20λ OF 0.2 X 10⁻⁶ M. SOLUTION OF
GLY+ALA+ALA-ALA C̄ NDA/CN AT:

pH = 9.5
$\lambda_{EXC}$ = 420nm
$\lambda_{EM}$ = 480nm
R = 0.01

ASSAYING METHOD FOR PRIMARY AMINES USING AROMATIC DIALDEHYDES

RELATED APPLICATIONS

This is a continuation-in-part of application Ser. No. 707,676, filed Mar. 4, 1985, now abandoned.

BACKGROUND OF THE INVENTION

1. Field of the Invention

The present invention relates to the fluorometric and electrochemical detection of low levels of primary amines and more particularly, to biogenic and endogenous amines such as catecholamines, amino acids, and peptides, by chemically converting the non-fluorescing amine of interest to an entity which is amenable to both fluorescent and electrochemical detection. Such is achieved by reacting fluorogenic reagents having an aromatic dialdehyde ring with the primary amine in the presence of a cyanide ion under mildly alkaline conditions. The invention further relates to the fluorometric and electrochemical detection of trace levels of cyanide.

2. Description of the Prior Art

Assaying techniques wherein a fluorogenic reagent is reacted with a substrate to form a fluorescing complex have been known for some time. One reagent used specifically for the derivatization of primary amines has been o-phthalaldehyde (OPA) which is of the formula:

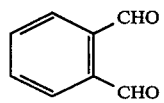

Under mildly alkaline conditions in the presence of a thiol, $R_1SH$ and a primary amine $R_2NH_2$, OPA forms 1-alkylthio-2-alkylisoindole (AAI), which is a highly fluorescent adduct of the formula:

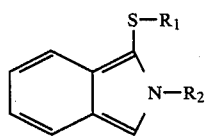

Although the fluorophores generated by the reaction of primary amines and OPA exhibit a relatively high fluorescent intensity with respect to many primary amines, it has been observed that the fluorescent intensity of the isoindole derivatives of primary amines containing an α-amido group are substantially lower. Thus, the OPA/thiol derivatizing system is not useful for the detection of femtomole quantities of peptides and proteins. Such represents a significant drawback of OPA for assaying many biological systems.

Another problem encountered with fluorogenic assaying techniques employing OPA relates to the relative instability of the 1,2-disubstituted isoindoles of certain amines such as glycine, γ-amino butyric acid (GABA), and β-alanine. These adducts have been observed to readily degrade into non-fluorescent products thereby placing severe time constraints on a practitioner when a concentration profile of the above amino acids is desired.

Naphthalene-2,3-dicarboxaldehyde (NDA) of the formula:

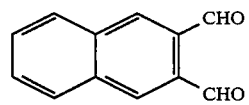

has also been used as a fluorogenic reagent. However, its use has been limited to the detection of arginine and arginine methyl ester and, even in that limited case, it is only very recently that the structure of the fluorescent reaction product has been characterized.

SUMMARY AND OBJECTS OF THE INVENTION

In view of the foregoing limitations and shortcomings of prior art assaying techniques as well as othe disadvantages not specifically mentioned above, it should be apparent that there still exists a need to the art for a method which enables assaying of trace concentrations of analytes containing one or more primary amino groups or trace levels of cyanide (CN). It is, therefore, a primary objective to fulfill that need by providing a process for assaying primary amines or cyanide wherein an aromatic dialdehyde is reacted with both cyanide ion and a primary amine in solution to yield an adduct which is detectable using fluorometric or electrochemical assaying techniques.

More particularly, it is an object of this invention to provide a process for assaying cyanide or biogenic and endogenous amines such as catecholamines, amino acids, and peptides.

It is a further object of the invention to provide an assaying process wherein the adducts formed are highly stable.

Yet another object of the invention is to provide an assaying process wherein the adducts formed exhibit a high degree of fluorescence, and thus are amenable to fluorometric techniques.

Still another object of this invention is to provide an assaying process wherein adducts formed undergo anodic oxidation at moderate potential and thus, are amenable to electrochemical detection techniques.

A further object of this invention is to provide a process for forming an adduct amenable to fluorometric and electrochemical assaying techniques from an aromatic dialdehyde, cyanide and a primary amine which satisfies the above as well as other objects.

Briefly described, these as well as other objects of the invention are achieved by providing a substituted or unsubstituted aromatic dialdehyde which reacts with primary amines and cyanide ions to form a fluorescent adduct which is amenable to detection by fluorometric and electrochemical techniques in amine concentrations as low as $10^{-12}$ moles/liter, and potentially even lower and with cyanide concentrations as low as $10^{-9}$ moles/liter.

With the foregoing and other objects, advantages, and features of the invention that will become hereinafter apparent, the nature of the invention may be more clearly understood by reference to the following detailed description of the invention, the appended claims and to the attached Figures.

DETAILED DESCRIPTION OF THE PREFERRED EMBODIMENTS

1. Preparation of Aromatic Dialdehydes

Figure 1:
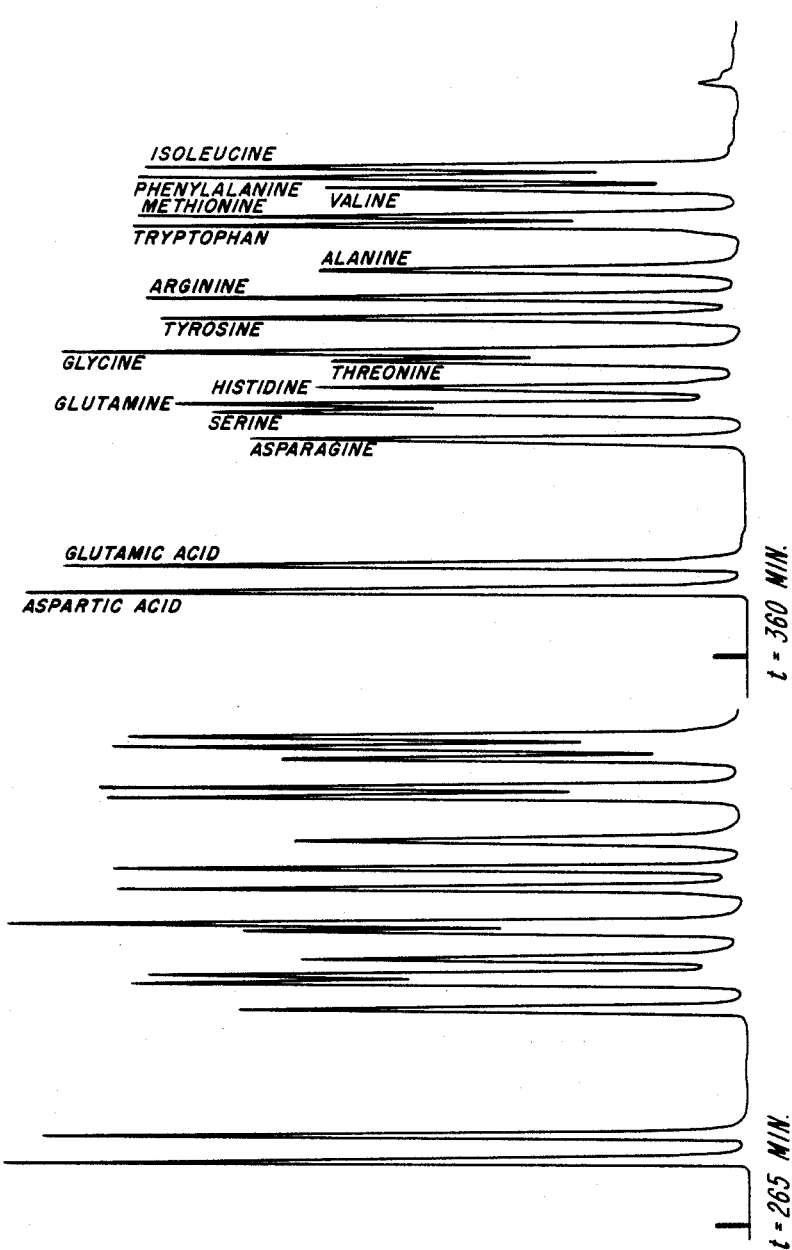
FIG. 1 depicts two chromatograms of an amino acid mixture taken 265 and 360 minutes after the derivatization reaction was initiated.

By the method of the present invention, a primary amine is reacted with an aromatic dialdehyde in the presence of cyanide ions. The aromatic dialdehydes may be selected from either substituted or unsubstituted o-phthalaldehydes (OPA) or naphthalene-2,3-dicarboxaldehydes (NDA). The naphthalene-2,3-dicarboxaldehydes are those of the formula:

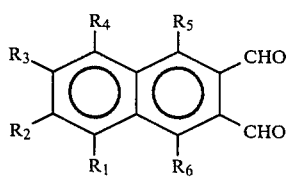

wherein:

(A) $R_1$ is H, $N(CH_3)_2$, $SO_3H$, $NO_2$, $SO_3^-Na^+$ or

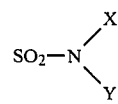

wherein X and Y are identical or different and are hydrogen or alkyl such as a $C_1$-$C_8$ alkyl and $R_2$, $R_3$, $R_4$, $R_5$, and $R_6$ are H; or (B) $R_1$, $R_4$, $R_5$, and $R_6$ are H, and

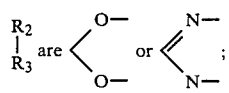

or (C) $R_1$ and $R_4$ are $N(CH_3)_2$ or

and $R_2$, $R_3$, $R_5$, and $R_6$ are H; or (D) $R_1$, $R_2$, $R_3$, and $R_4$ are H and $R_5$ and $R_6$ are $OCH_3$,

$OSi(CH_3)_2 C_4H_9$, or $N(CH_3)_2$; or (E) $R_1$, $R_4$, $R_5$, and $R_6$ are H and $R_2$ and $R_3$ are $CH_3O$,

$SO_3H$, or $CO_2H$, or the salts thereof; or (F) $R_1$, $R_3$, $R_4$, $R_5$, and $R_6$ are H and $R_2$ is $(CH_3)_2N$.

In a preferred embodiment, the substituted or unsubstituted naphthalene -2,3-dicarboxaldehyde is of the formula:

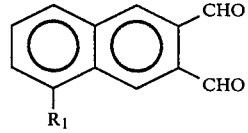

wherein $R_1$ is H, $N(CH_3)_2$, $SO_3H$, $NO_2$, or $SO_3^-Na^+$.

Unsubstituted naphthalene-2,3-dicarboxaldehyde of the formula:

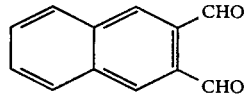

is a known compound and was prepared by the following alternative sequences:

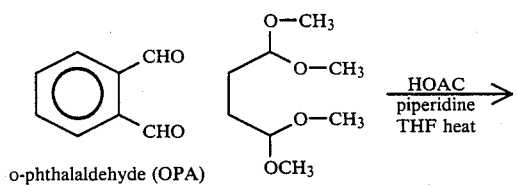

o-phthalaldehyde (OPA)

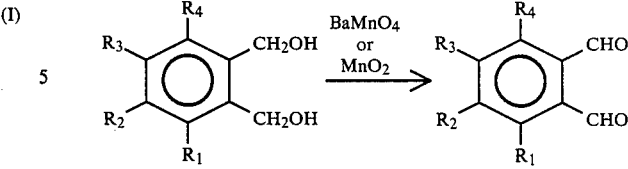

(I)

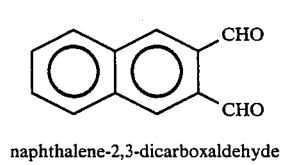

naphthalene-2,3-dicarboxaldehyde

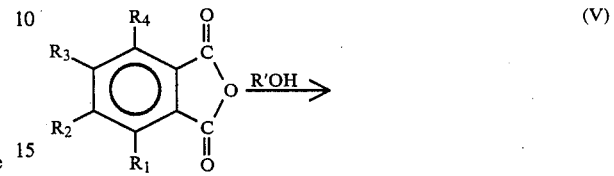

(V)

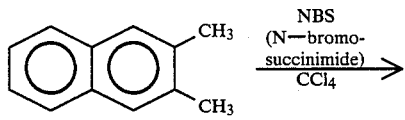

(II)

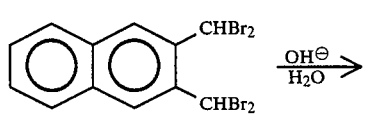

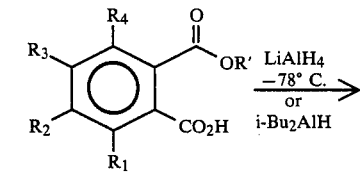

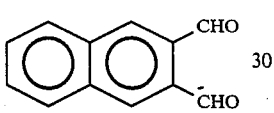

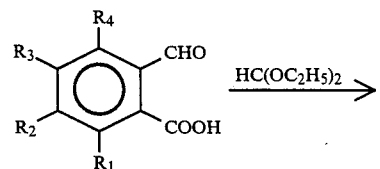

The latter process is reported by W. Ried and H. Bodem in Chem. Ber., Vol. 89, p. 708 (1956).

The substituted naphthalene-2,3-dicarboxaldehydes are prepared by forming a suitably substituted o-phthalaldehyde for use in reaction (I) above. Thus, $R_1$, $R_2$, $R_3$, and $R_4$ substituents of the NDA can be selected by reacting similarly substituted o-xylene or phthalic anhydride as precursors to o-phthalaldehyde according to the following sequences:

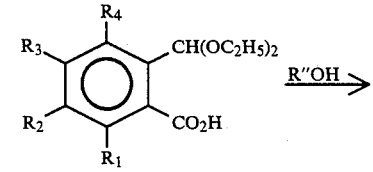

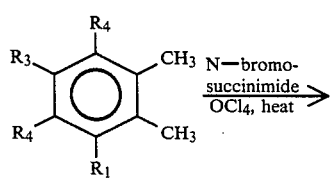

(III)

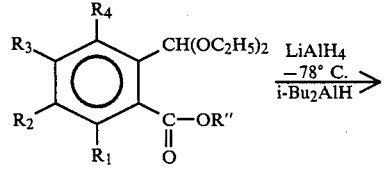

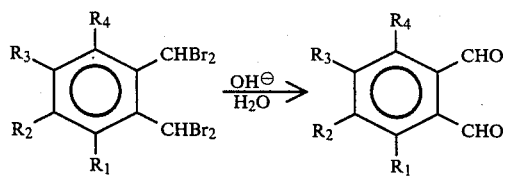

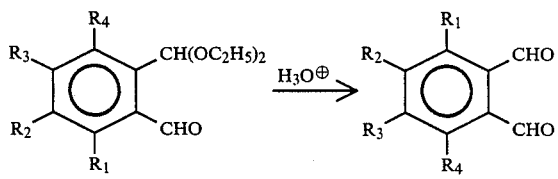

In addition to substituted (such as di- or tetra- substituted) or unsubstituted naphthalene-2,3-dicarboxaldehydes, it is also possible to use as a starting reagent several heterocylic dialdehyde and analogs such as those of the formulae:

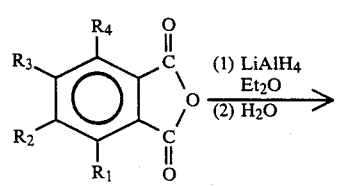

(IV)

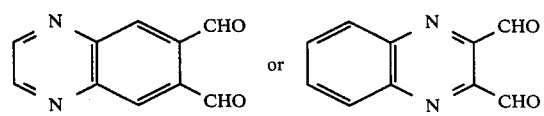

Finally, it will be appreciated that the rings may be substituted at the $R_5$ and $R_6$ positions by conventional ring addition techniques well known to those skilled in the art.

Alternatively, the starting material may be ophthalaldehyde of the formula:

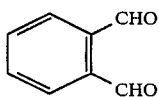

As is the case with naphthalene-2,3-dicarboxaldehyde, ophthalaldehyde is a known is a known compound readily available or prepared by persons skilled in the art. Persons skilled in the art will appreciate that the OPA may be substituted at the 4 and 5 positions with substituents which are capable of enhancing the stability and fluorescence quantum of the isoindole product. As non-limiting examples are methoxy and dimethylamino substituents.

2. Formation of the Adducts Amenable to Fluorometric on Electrochemical Assaying Techniques In order to assay primary amine compounds, the NDA or OPA compounds described above and controlled amounts of cyanide are reacted with the analyte to form the adducts amenable to fluorometric or electrochemical assaying techniques. Conversely, in order to assay trace levels of cyanide, the NDA or OPA compounds described above are reacted with cyanide in the presence of controlled amounts of primary amines to form the adducts amenable to fluorometric or electrochemical assaying techniques. The adducts are formed as follows:

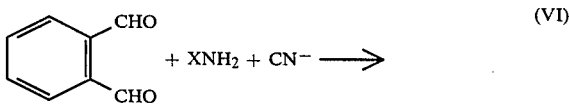

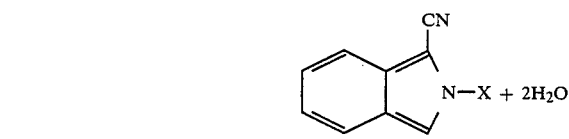

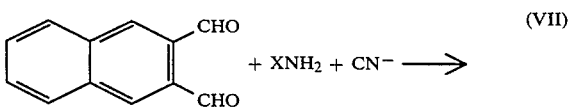

X— is a radical derived from a primary amine of the formula X—$NH_2$. Included within the definition of X—$NH_2$ are peptides, amino acids and catecholamines.

In order to assay cyanide, the sample containing the cyanide to be determined is added to a freshly prepared solution containing 0.1–0.5 micromolar aromatic discarboxaldehyde and 0.1–1.0 micromolar primary amine in a buffered pH-controlled solution (pH 7–10) at a temperature preferably ranging from 25° to 40° C. After enough time has passed so as to enable the reaction to go substantially to completion, which is generally 10 minutes to 1 hour, the concentration of cyanide can be determined by measuring the amounts of adducts in the solution using high performance liquid chromatography with fluorescence or chemiluminescence detection. The optimal wavelengths for excitation of the products produced from OPA are 230 and 330 nm and the optimal wavelength for emission is about 450 nm. With respect to the CBI adducts produced from the NDA and cyanide compounds, the optimal excitation wavelengths are 250, 420 and 440 nm whereas the optimal emission wavelength is about 490 nm.

By virtue of the above-described process, it is possible to quantify nanomolar concentrations of cyanide.

In order to assay primary amines, using substituted or unsubstituted NDA compounds, a 100 to 5000 micromolar solution of NDA was combined with a 50 to 100 micrometer solution of cyanide such as KCN or NaCN in the presence of a 10 to 500 millimolar borate buffer solution. For such an NDA/CN reagent system, the excitation and emission wavelengths were 420 and 490 nm, respectively. These conditions are merely illustrative, and one skilled in the art will appreciate that conditions may be varied without affecting the adduct formation.

When the above adducts were fluorophores and were fluorometrically analyzed, it was observed that assaying could be carried out with as little as 50 femtomoles of analyte.

The adducts of the present invention are also amenable to electrochemical analytical techniques.

In detecting primary amines using OPA, preferably 0.05 to 0.5 millimolar OPA and 0.05–1.0 millimolar cyanide are reacted with the primary amine and analyte in an aqueous buffered solution having a pH ranging from 7–10 and a temperature of about 25° C. The preferred excitation and emission wavelengths of the adduct are 330 and 450 nm respectively. Detection of sub-picomole levels of primary amines is possible by virtue of this process.

The separating step, such as by high performance liquid chromatography (HPLC) may be carried out before or after the reacting step.

When the mono-substituted OPA or NDA derivatives are used with a mixture of primary amines before the separating step, such as (HPLC), it is possible that two peaks will be observed for each primary amine analyte due to the formation of isomers as shown by the following:

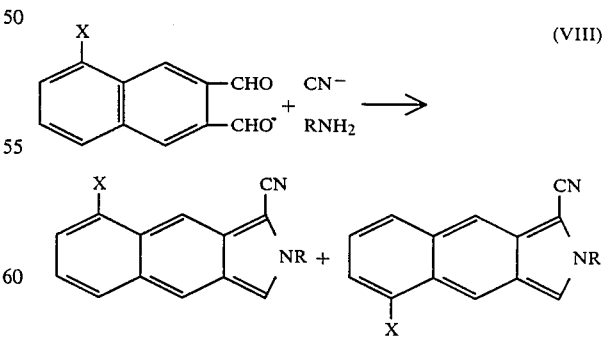

Since it is undesirable to obtain two peaks for each analyte in the chromotographic system, it is preferred to maintain the symmetry of the fluorogenic reagents through di- or tetrasubstitution wherein $R_1$ and $R_4$, $R_2$ and $R_3$, and $R_5$ and $R_6$ are identical. The same phenomena occurs with OPA derivates which form two isomers as follows:

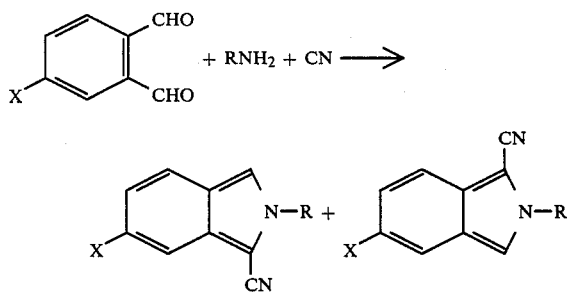

The invention will be further clarified by a consideration of the following examples, which are intended to be purely exemplary of the use of the invention.

EXAMPLE 1

Sixteen amino acids derivatized with naphthalene2,3-dicarboxaldehyde

Into a low actinic 10-ml volumetric flask were added 9.6 ml of a 1.0 molar solution of sodium borate followed by the addition of 100 microliters of a $1 \times 10^{-4}$ M solution of the following 16 amino acids:
glycine
alanine
tyrosine
valine
phenylalanine
aspartic acid
serine
glutamic acid
histidine
threonine
isoleucine
methionine
tryptophan
arginine
asparagine
glutamine Next, 100 microliters of 0.05 M NaCN and 200 microliters of 0.01 M NDA in methanol were added. The solution was thoroughly mixed and placed in a 25° C. water bath.

A Kratos FS-970 fluorescence detector was used to measure fluorescence. The excitation wavelength was 420 nm and the emission intensity was monitored using a 470 nm cut off filter. An Hypersil ODS 5 $\mu$m column was also used. The gradient was 15-55% CH$_3$CN in phosphate buffer. Solvent A (Mobile Phase) was 15% CH$_3$CN and 85% 0.05 M PO$_4$ at a pH of 6.8. Solvent B was 55% CH$_3$CN and 45% 0.05 M PO$_4$ at pH of 6.8.

A chromatogram of the mixture was taken after 265 and 360 minutes and is shown at FIG. 1. The profiles after such time periods demonstrates the stability of the adducts of the present invention.

EXAMPLE 2

Aspartame Derivatized with Naphthalene-2,3-Dicarboxaldehyde

Figure 2:
FIG. 2 depicts three chromatograms of a solution of 1-cyano-benz[f]isoindole (CBI) derivative of aspartame analyzed at different time intervals.

A solution containing about 1 mg/ml of the CBI derivative of aspartame in borate buffer at a pH of 9.5 was analyzed by HPLC-UV (254nm) using a Waters 10$\mu$ column, an injection volume of 20 microliters, and a mobile phase comprised of 30% CH$_3$CN in H$_2$O. Two peaks were observed (See FIG. 2), one of which increased with time and the other of which decreased with time. Without being limited by theory, it is believed that hydrolysis of the methyl ester of the dipeptide occurs since the second peak (the most hydrophobic) is the one decreasing with time.

EXAMPLE 3

Figure 3:
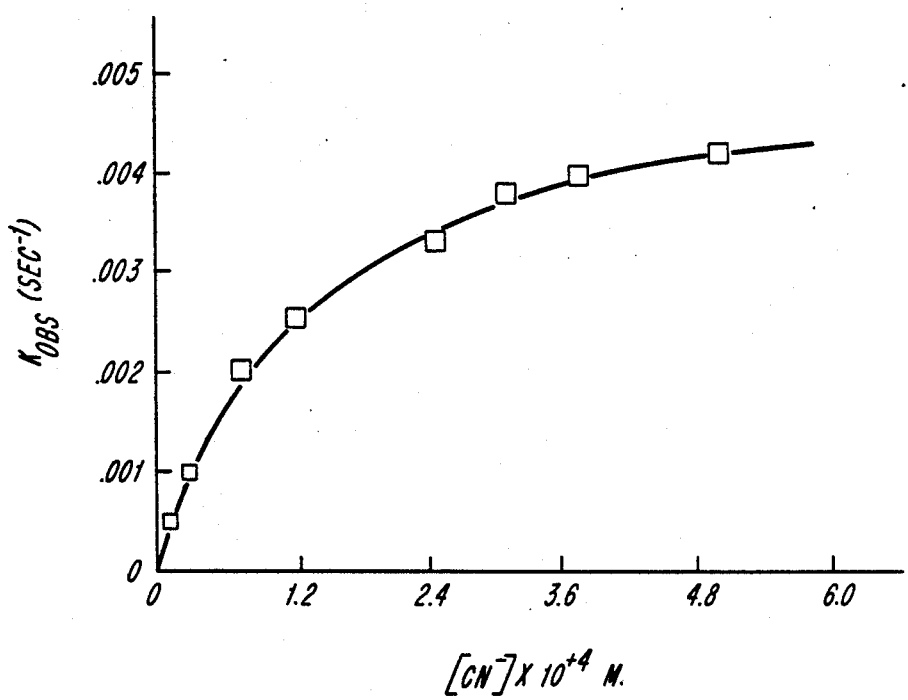
FIG. 3 is a graph depicting the dependence of the pseudo-first order rate constant for the formation of the CBI derivative of alanine upon the effective concentration of cyanide.
Figure 4:
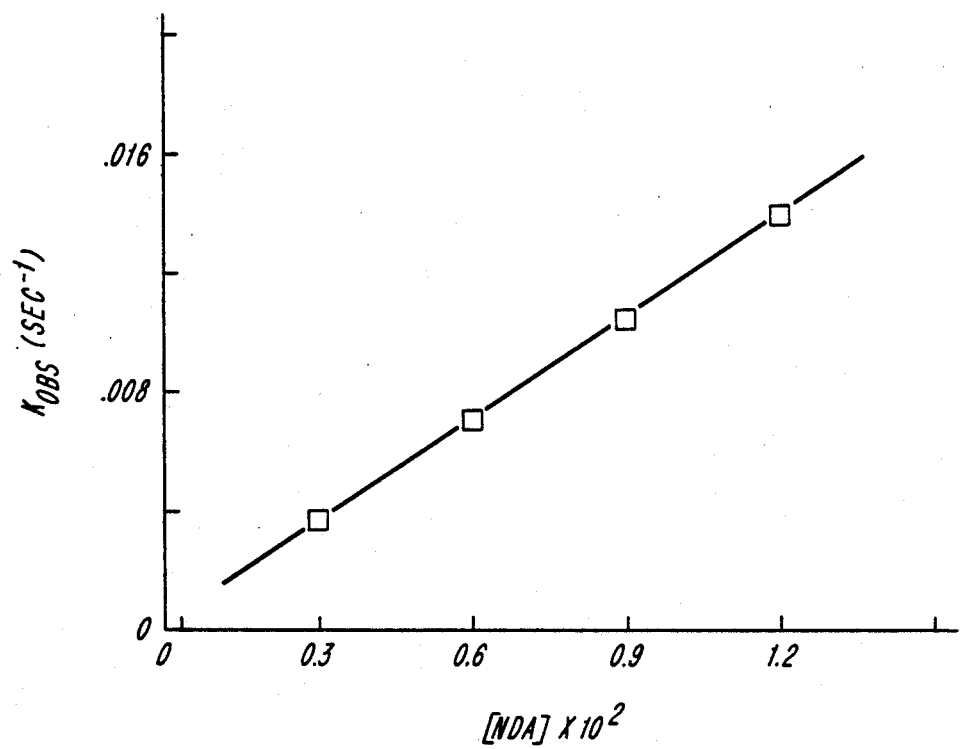
FIG. 4 is a graph depicting the dependence of the pseudo-first order rate constant for the formation of the CBI derivative of alanine upon the concentration of NDA.

Dependence fo the Observed Reaction Rate Constant (kobs) on the Effective Concentration of Cyanide and NDA A $2.0 \times 10^{-4}$ M solution of NDA was combined with a $2.0 \times 10^{-6}$ M solution of alanine in the presence of varying concentrations of cyanide. The pH of the mixture was 9.5 in a borate buffer at 25° C. and an ionic strength of 0.1. A graph of this relationship is shown in FIG. 3. The same determination of $k_{obs}$ was made with respect to the NDA concentration. Once again, the pH was 9.5, the reaction temperature 25° C., and the ionic strength 0.1. However, the concentration of cyanide and alanine were $1.0 \times 10^{-3}$ M and $2.0 \times 10^{-6}$ M respectively. The relationship is shown at FIG. 4.

EXAMPLE 4

Figure 5:
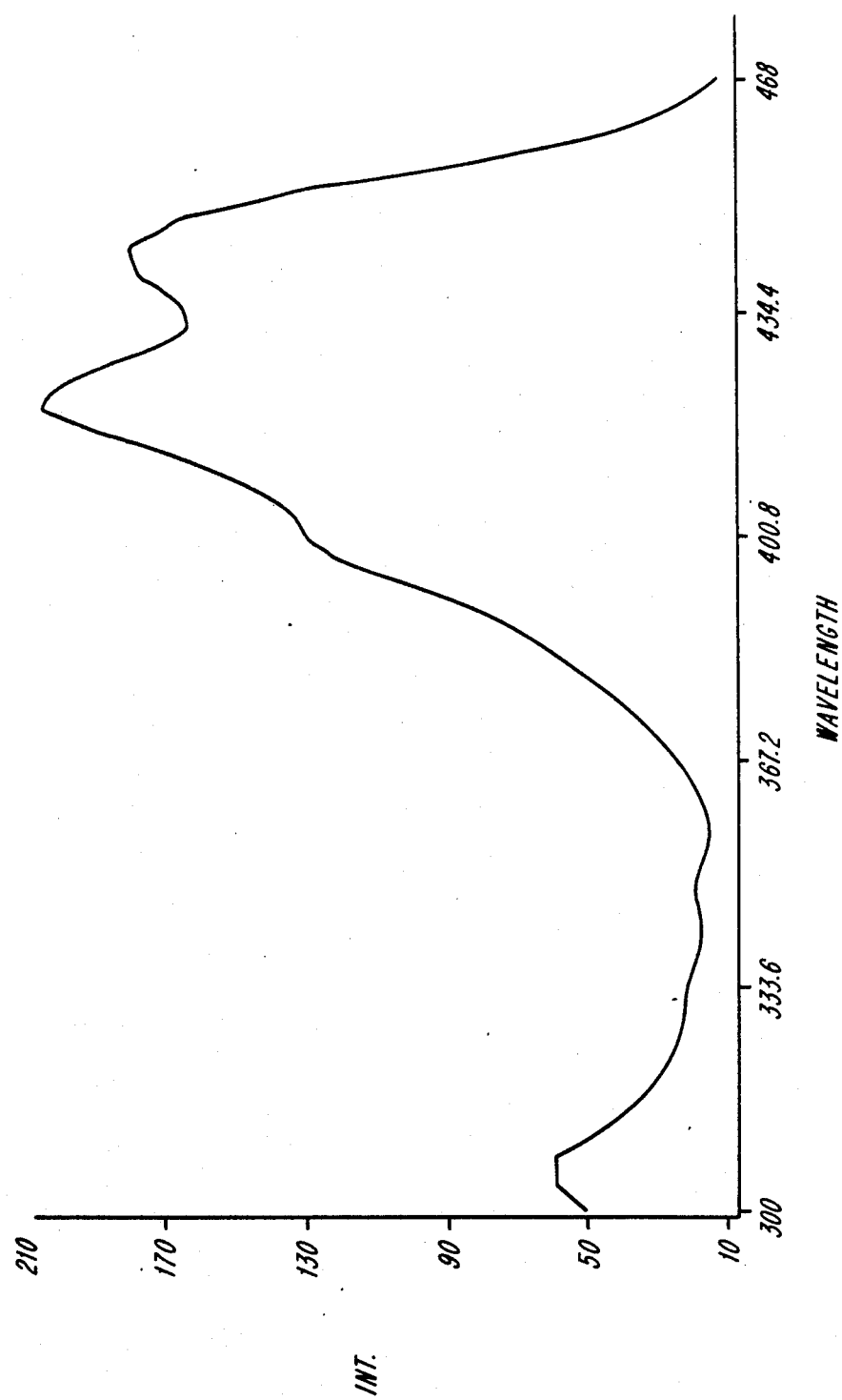
FIG. 5 depicts the excitation spectrum of the CBI derivative of alanine.
Figure 6:
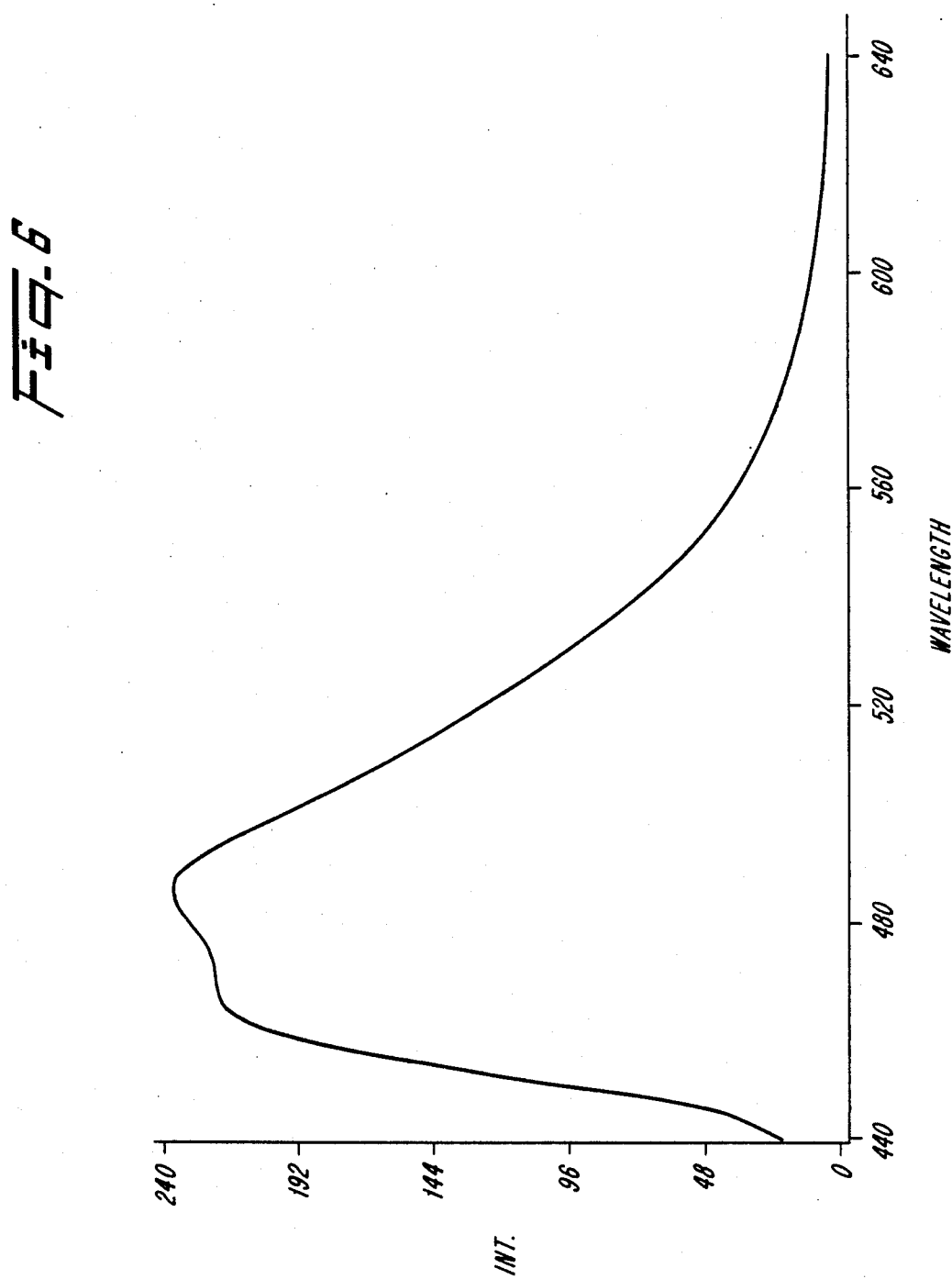
FIG. 6 depicts the emission spectrum of the CBI derivative of alanine.

Determination of the Relative Fluorescent Intensities for the Analysis of Alanine with NDA in the Presence of Cyanide In a quartz cuvette were added 100 microliters of 60 micromolar alanine solution followed by 100 microliters of 0.01 M NDA and 0.1 M NaCN in water. The relative fluorescent intensities of the excitation and emission spectra are shown in FIGS. 5 and 6 respectively.

EXAMPLE 5

Determination of the optimum pH for the NDA/CN Reaction with Alanine

Figure 7:
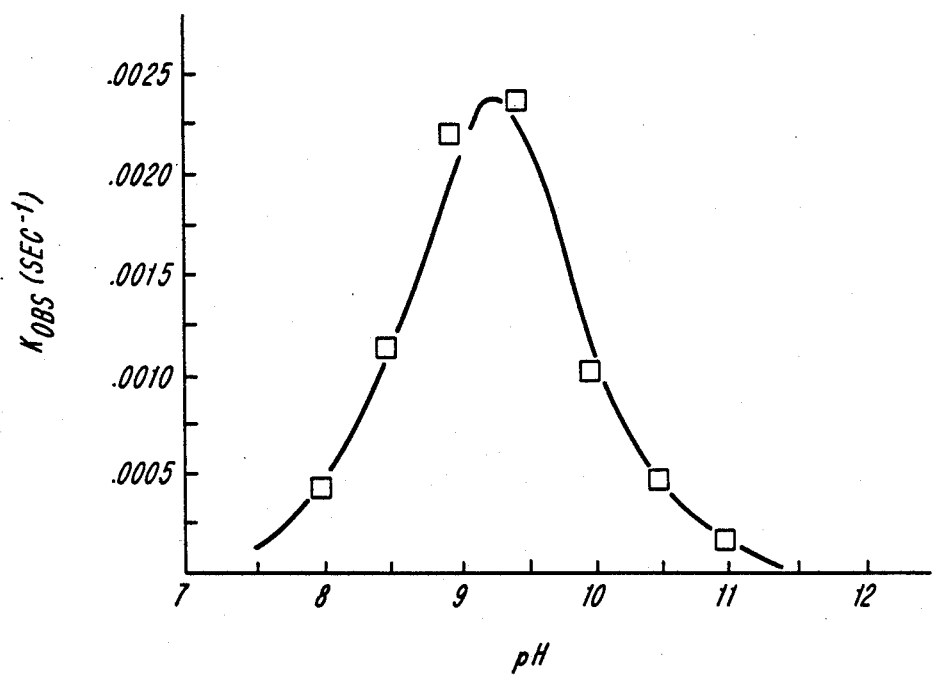
FIG. 7 is a graph depicting the dependence of the first-order rate constant $k_{OBS}$ for the reaction of alanine with NDA and CN upon the pH.

Table 1 lists the first-order rate constants, $k_{obs}$, for the formation of the CBI derivative of alanine as a function of pH. A plot of $k_{obs}$ versus pH shows a maximum reaction rate at pH 9.5 (FIG. 7) which is analogous to the o-phthalaldehyde/2-mercapatoethanol reagent system. The reaction was carried out at 30 C. The concentrations of NDA, CN, and alanine were $2.0 \times 10^{-4}$ M, $2.0 \times 10^{-4}$ M and $1.0 \times 10^{-6}$ M, respectively.

TABLE 1

FIRST-ORDER RATE CONSTANTS FOR THE REACTION OF NDA WITH ALANINE AND CYANIDE AT 30° C., [NDA] = 0.20 mM, [CN] = 0.20 mM AND [ALA] = 1.0 uM, pH MAINTAINED BY pH-STAT, IONIC STRENGTH = 0.1

| pH | $10^4 k_{obs}, s^{-1}$ |
|---|---|
| 8.0 | 4.9, 3.5 |
| 8.5 | 11.2, 10.6 |
| 9.0 | 22.3, 21.4 |
| 9.5 | 24.4, 22.4 |
| 10.0 | 8.9, 10.4 |
| 10.5 | 5.5, 3.6 |
| 11.0 | 2.0, 1.1 |

EXAMPLE 6

Figure 8:
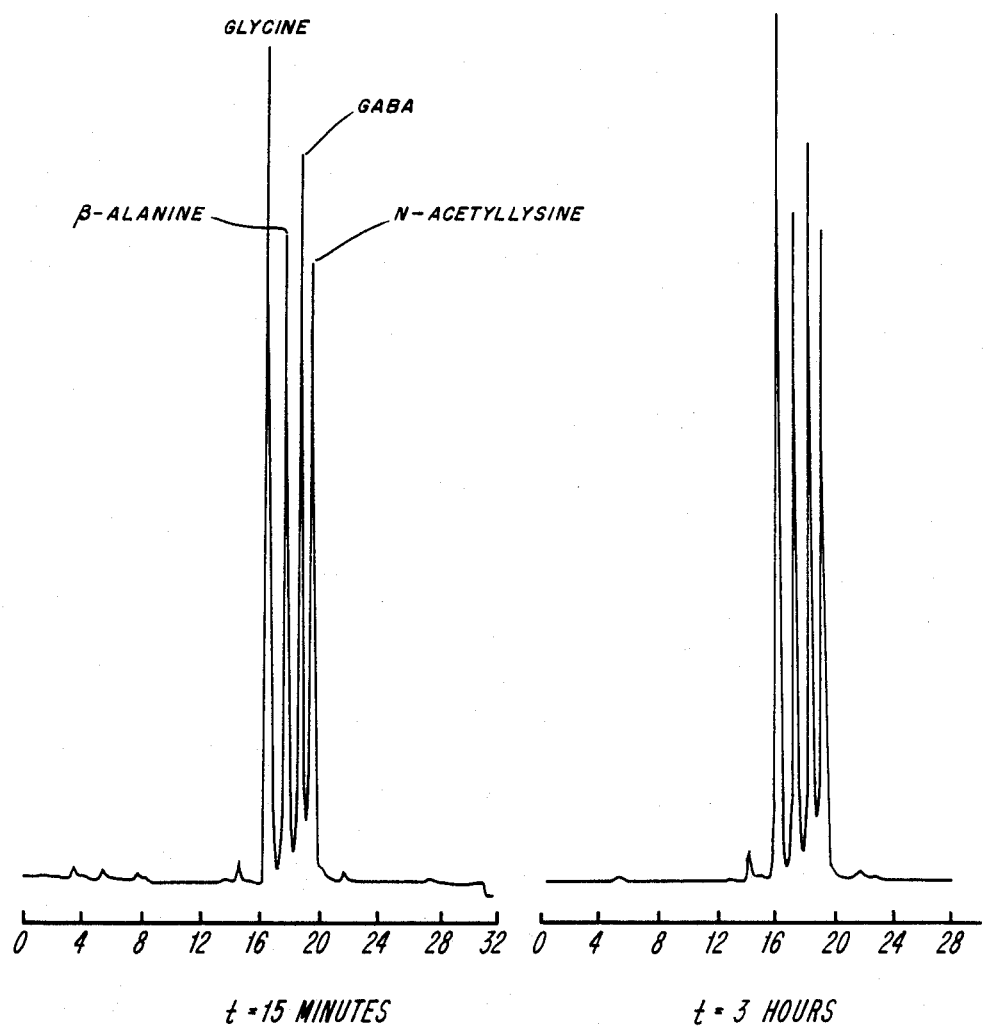
FIG. 8 is a chromatogram depicting the elution profiles of the reaction products of four amino acids with NDA and CN after a reaction time of 15 minutes (A) and 3 hours (B)

Influence of Reaction Time of the NDA/CN reaction on the fluorescence Intensity of Four Amino Acid CBI Derivatives A $10^{-4}$ M solution of glycine, β-alanine, GABA, and N-α-acetyl-lysine were reacted wtih a 0.01 M solution of NDA and 0.05 M CN⁻ to yield in 0.1 M borate buffer at pH 9.3, $10^{-6}$ M of the fluorophores. 50 microliters were then injected onto the HPLC system with fluorescence detection (range=0.5 μA full scale). Separation was performed using a linear gradient over 30 minutes from 15% $CH_3CN$ to 55% $CH_3CN$ in 0.05 M phosphate buffer at a pH of 6.8. The elution profiles after a reaction time of 15 minutes and 3 hours are shown in FIG. 8. As can be seen from FIG. 8, little or no degradation of the reaction products of the four amino acids with NDA and CN was observed after 3 hours at a pH of 9.3.

EXAMPLE 7

Figure 9:
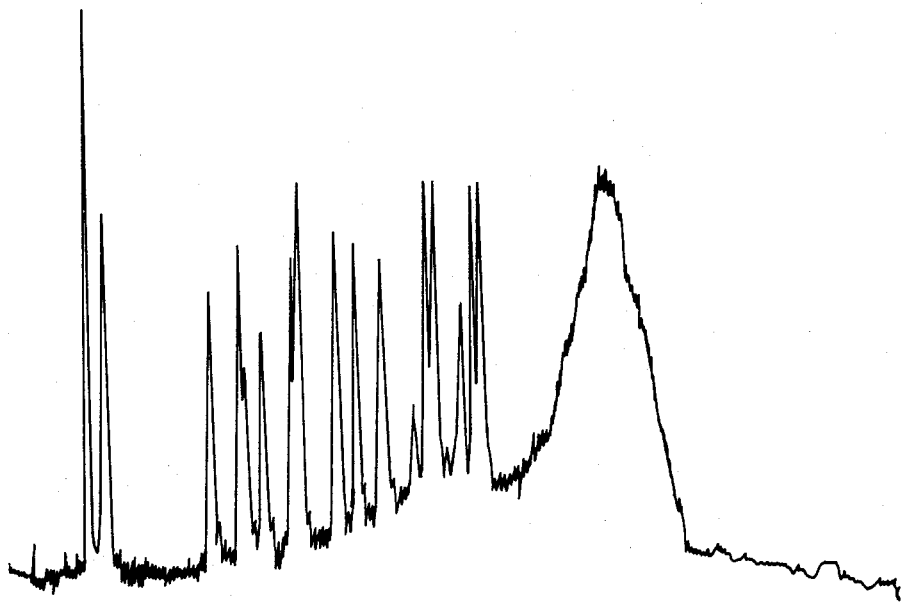
FIG. 9 is a chromatogram depicting the elution of CBI derivatives of sixteen amino acids.

Determination of the Detection Limit for the Analysis of 16 Amino Acids with NDA/CN 50 microliters of $10^{-4}$ M of a mixture of 16 amino acids were derivatized by reacting them with 50 microliters of 0.05 M NaCN and 100 μl of 0.01 M NDA for 2 minutes. This solution mixture was then diluted to give a $10^{-8}$ M solution of amino acids. A 50 microliter aliquot of the solution was then injected onto the HPLC, i.e., 500 femtomoles. The column was an ODS-Hypersil, 5 μm particles, 4.6 (i.d.)×150 mm. The guard column was 4.6×150 mm. The mobile phases were (A) 15% $CH_3CN$/85% phosphate buffer, (0.05 M, pH 6.8) and (B) 55% $CH_3CN$/45% phosphate buffer, (0.05 M, pH 6.8). The gradient profile was linear changing from 100% A to 100% B in 60 min. The flow rate was 1.0 ml/min. A Kratos fluorescence detector FS-970 was used. The excitation wavelength was 246 nm and a 470 nm emission cut off filter was used. The time constant was 6 seconds and the range was 0.2 μA. The chromatogram is shown in FIG. 9.

EXAMPLE 8

Eighteen amino acids derivatized with naphthalene-2,3-dicarboxaldehyde

The following 18 amino acids were derivatized with NDA and CN:
(1) cysteic acid
(2) aspartic acid
(3) glutamic acid
(4) asparagine
(5) histidine
(6) glutamine
(7) serine
(8) arginine
(9) glycine
(10) threonine
(11) alanine
(12) tyrosine
(13) valine
(14) methionine
(15) tryptophan
(16) isoleucine
(17) phenylalanine
(18) leucine An aliquot (50 μl) of the amino acid mixture ($1.0 \times 10^{-5}$M) was mixed with 200 μl of borates buffer (0.01 M, pH=9.1) followed by the addition of 200 μl of NDA ($1 \times 10^{-3}$M) and 50 μl of sodium cyanide ($1 \times 10^{-2}$M). After 15 minutes, a 50 μl aliquot was injected (i.e. 5–50 picomoles) onto the HPLC for quantification.

Solutions were injected onto an Ultrasphere ODS column (5μm, 250×4.6mm.i.d., Rainin Instruments (Woburn, MA., U.S.A.)) attached to an Hypersil ODS guard column (5μm, 50×4.6mm.i.d., Shandon Southern (Sewickley, Pa.)) packed in our laboratory. The elution was performed using isocratic mode for the pH-rate profile study using a mobile phase consisting of 25% acetonitrile and 75% phosphate buffer (0.05M, pH 6.8). The gradient was done by the application of a solvent gradient provided by two Altex pumps (model 110A, Beckman Instruments, Berkeley, Calif.). Solvent A was 10% THF with 90% phosphate buffer (0.05M, pH 6.8), and solvent B was 55% acetonitrile with 10% methanol and 35% phosphate buffer (0.05M, pH 6.8). The eluant was monitored using a Model FS 970 LC fluorometer (Schoeffel Instruments) equipped with Corning 7-54 primary filter and a 470 nm cutoff secondary filter. The excitation wavelength was set to 420 nm. The cell volume was 5 μl. The range was set at 1.0 μA., and the time constant at 0.5 sec. Quantification was accomplished with an Omniscribe recorder by manual peak height measurements. A linear gradient profile was employed from 0 to 60% B over the period of 60 minutes followed by a steep increase to 100% B over a period of 5 minutes. At the end of the run, the eluant was returned to 100% A over a period of 5 minutes. The gradient was controlled by a SLIC 1400 (Systec. New Brighton, Minn.). A total flow rate of 1.0 ml/min was used throughout.

Figure 14:
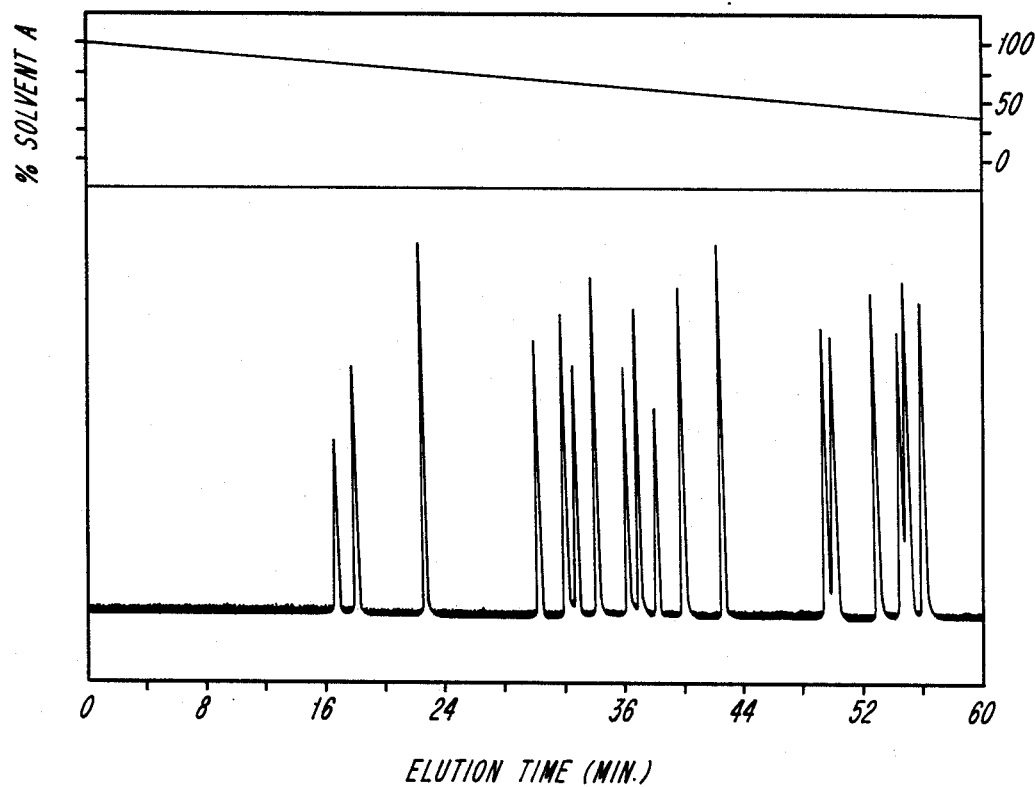
FIG. 14 is a gradient elution profile consisting of the mixture of eighteen amino acids derivatized with NDA and CN.

A gradient elution profile consisting of the mixture of 18 amino acids derivatized with NDA and CN appears in FIG. 14. Each peak on this chromatogram represents 20 picomoles injected onto the HPLC column, except for arginine which represents 10 picomoles.

TABLE 2

Between run precision of the methodology (see gradient elution study in material and methods)*.

| | | Standard curve | |
|---|---|---|---|
| Peak | Amino Acid | slope | (n = 4)S.D. |
| 1 | Cysteic acid | 1.57 | 0.11 |
| 2 | Aspartic acid | 2.15 | 0.17 |
| 3 | Glutamic acid | 2.91 | 0.18 |
| 4 | Asparagine | 2.25 | 0.12 |
| 5 | Histidine | 2.12 | 0.12 |
| 6 | Glutamine | 2.22 | 0.15 |
| 7 | Serine | 2.54 | 0.12 |
| 8 | Arginine | 1.93** | 0.14** |
| 9 | Glycine | 2.41 | 0.16 |
| 10 | Threonine | 1.78 | 0.16 |
| 11 | Alanine | 2.42 | 0.15 |
| 12 | Tyrosine | 2.71 | 0.13 |
| 13 | Valine | 2.29 | 0.09 |
| 14 | Methionine | 2.10 | 0.09 |
| 15 | Tryptophan | 2 24 | 0 27 |
| 16 | Isoleucine | 2.24 | 0.09 |
| 17 | Phenylalanine | 2.54 | 0.11 |
| 18 | Leucine | 2.30 | 0.11 |

*The standard calibration curves were plotted by correlating the fluorescence response (peak height) versus the amount injected onto the HPLC (5–50 picomoles).
**The amount of the amino acid arginine injected varied between 2.5 and 25 picomoles.

EXAMPLE 9

Electrochemical Detection of the CBI and isoindole derivatives of alanine

The following three standard solutions were prepared:

(A) CBI derivative of alanine (conc. = $10 \times 10^{-5}$M) in borate buffer (pH 9.5), 50 μL of this solution being injected onto the HPLC column;

(B) methyl hydroquinone (5 microgram/ml) in HPLC grade methanol; 50 μL of this solution was injected onto the HPLC column;

(C) 1-(2-mercaptoethanol)-isoindole of alanine formed in situ by reacting 100 microliters of alanine (0.005 M) with 200 microliters of 2-mercaptoethanol (0.25%) and 100 microliters of OPA (0.01 M) in borate buffer (pH 9.5) to give a final volume of 10.0 ml. Ten microliters of this solution were injected onto the HPLC column.

The aliquots of the stock solutions (A)–(C) were subjected to HPLC as follows:
Column: Hypersil ODS (15 cm×46 mm i.d.)
Mobile Phase:
(A) 25% CH$_3$CN/75% phosphate buffer (0.1 M, pH 6.8)
(B&C) 18% CH$_3$CN/82% phosphate buffer (0.1 M, pH 6.8)
Flow Rate: 1.0 ml/min
Detector: Model 5010 Standard ESA analytical cell consisting to two porous graphite coulometric electrodes.

Figure 15:
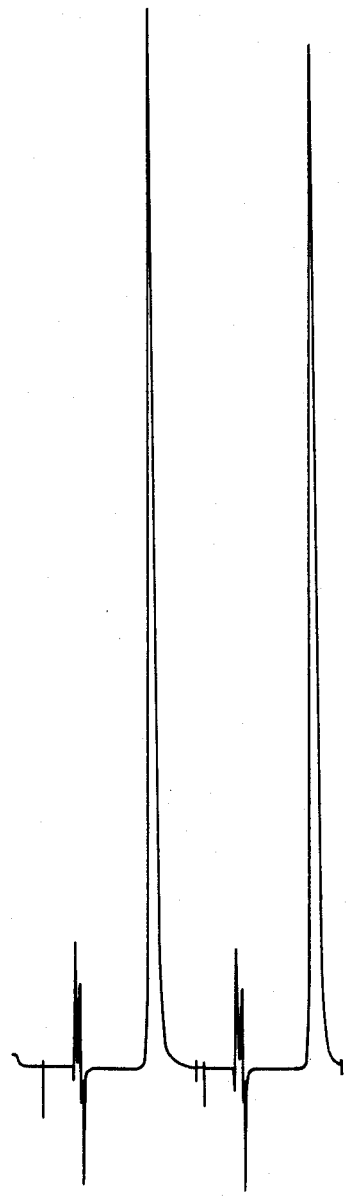
FIG. 15 is a chromatogram of a 50 microliter injection of a CBI derivative of alanine stock solution ($1 \times 10^{-5}$M) in borate buffer using an electrochemical detector with an applied potential of 0.28V.

A chromatogram of a 50 microliter injection of the CBI derivative of alanine solution ($1 \times 10^{-5}$ M) in borate buffer at an applied potential of +0.28V (vs. H$_2$/H$^+$) is shown in FIG. 15. The voltamograms were generated by injecting an aliquot of the same concentration of each compound (A, B and C) at different applied potentials. Peak heights translated to microampere (μA) were plotted against the applied potential (volts).

COMPARATIVE EXAMPLE 1

Figure 10:
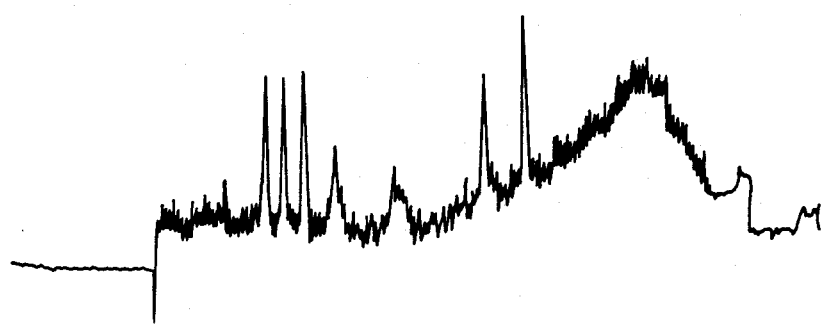
FIG. 10 is a chromatogram depicting the elution of the reaction products of sixteen amino acids with ophthalaldehyde and 2-mercaptoethanol (2ME)

500 femtomoles of the adduct of the reaction of OPA and 2ME with the same 16 amino acids analyzed in Example 7 were likewise subjected to an identical HPLC separation. The concentration of OPA was $1.8 \times 10^{-6}$ M whereas the concentration of 2-mercaptoethanol was $10 \times 10^{-6}$ M. The reaction was carried out in a 0.1 M sodium borate solution and the adducts fluorometrically analyzed at an excitation wavelength of 230 nm and an emission wavelength of greater than 418 nm. The chromatogram is shown at FIG. 10.

COMPARATIVE EXAMPLE 2

Figure 11:
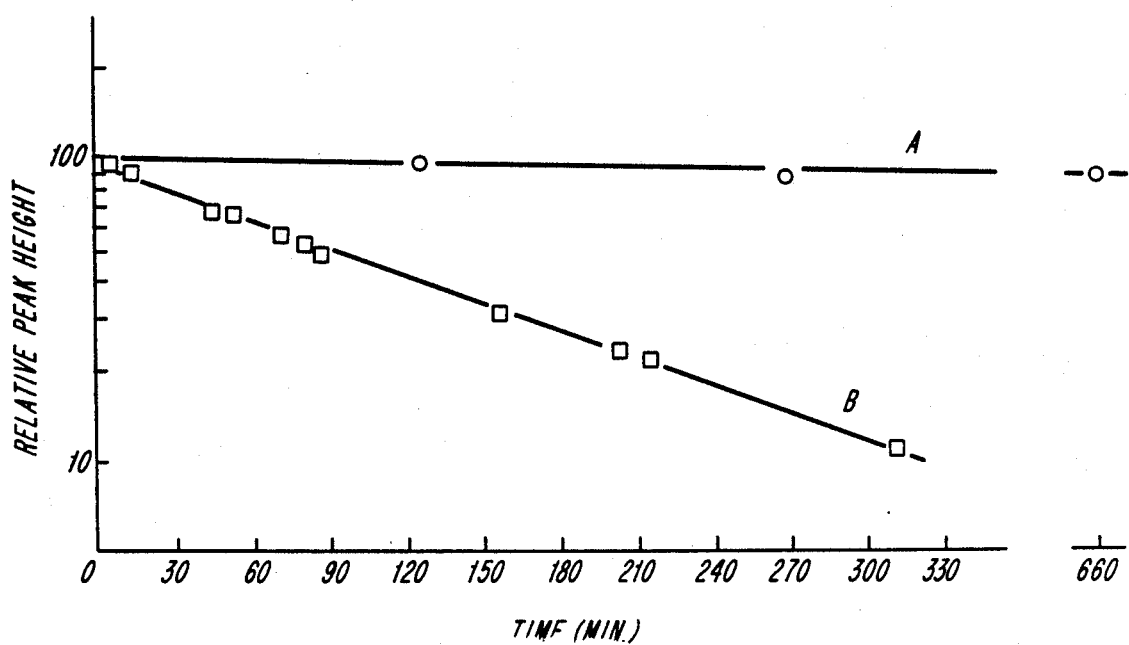
FIG. 11 is a degradation profile of the CBI derivative of glycine and the 1-(2-mercaptoethanol)-isoindole of glycine in a mixed solvent.

The degradation profiles of (A) CBI derivative of glycine and (B) 1-(2-mercaptoethanol)-isoindole of glycine were compared. The adducts were analyzed in a mixed solvent, protected from light, consisting of 20% methanol and 80% borate buffer (conc.=0.1 M, pH=9.5). The mixture was maintained at 25° C. and monitored by HPLC. As shown in FIG. 11, the adducts of the present invention are far more stable than those obtained with OPA.

COMPARATIVE EXAMPLE 3

Figure 12:
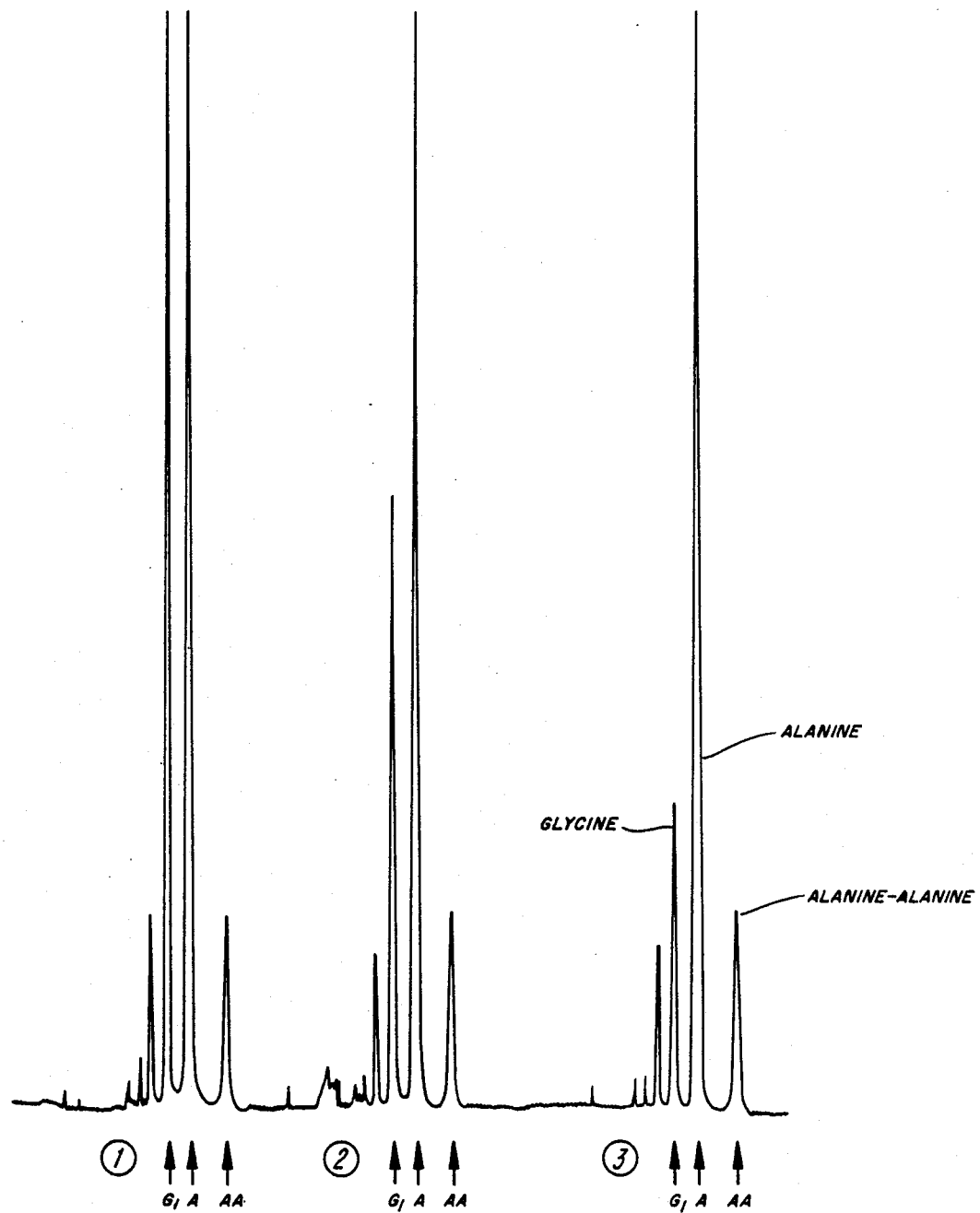
FIG. 12 depicts three chromatograms of the reaction product of OA and 2ME with two amino acids and one dipeptide at different time of reaction.
Figure 13:
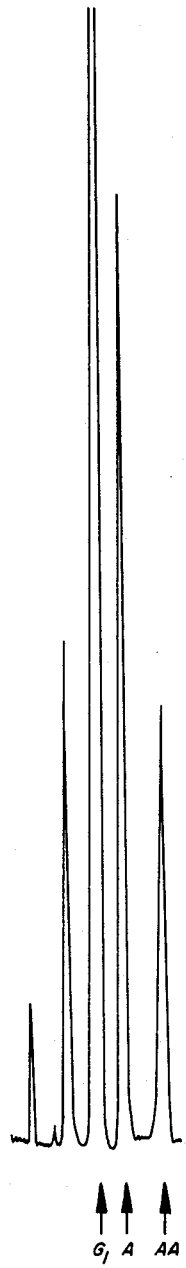
FIG. 13 is a chromatogram of the reaction product of NDA and CN with two amino acids and one peptide.

The detection limits of the OPA-2ME method versus the NDA-CN method were again compared. An LKB 2151 variable wavelength monitor (Absolute wavelength of 335 nm for OPA and 420 nm for NDA); a Farrand optical spectrofluorometer (OPA excitation and emission wavelengths of 335 and 430 nm and NDA excitation and emission wavelengths of 420 and 480 nm) and a Rheodyne injector (20 microliter loop) were used. An LKB 2152 HPLC controller, an LKB 2150 HPLC pump and an LKB 2210 HPLC recorder were also used. The mobile phase for the OPA/2ME adducts was 18% acetonitrile (CH$_3$CN) : 82% 0.05 M phosphate buffer (pH 6.8). The mobile phase for the CBI derivatives was 25% CH$_3$CN : 75% 0.05 M phosphate buffer (pH of 6.8). The results are shown in FIGS. 12 and 13 where a 20 picomole injection of glycine, and alanylalanine admixed with OPA/2ME at pH 9.5, excitation wavelength of 335 nm, and emission wavelength of 430 nm (range=0.01μA) are compared with a 4 picomole injection of the same amino acids admixed with NDA/CN at pH 9.5, with an excitation wavelength of 420 nm and an emission wavelength of 480 nm (range=0.01μA).

Thus, in terms of detectability and stability, the NDA/CN and OPA/CN adducts of the present invention are far superior to the OPA/2ME system of the prior art.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method of assaying primary amines comprising the steps of:
   (i) reacting a reagent that is reactive with primary amines and cyanide with cyanide ions and at least one primary amine to form an adduct amenable to fluorometric or electrochemical assaying techniques, wherein the reagent is a substituted or unsubstituted naphthalene-2,3-dicarboxyaldehyde or o-phthalaldehyde; and
   (ii) fluorometrically or electrochemically assaying said adduct.

2. The method of claim 1 wherein the reagent is such that said adduct is a fluorophore.

3. The method of claim 1 wherein said reagent is a substituted or unsubstituted naphthalene-2,3-dicarboxaldehyde of the formula:

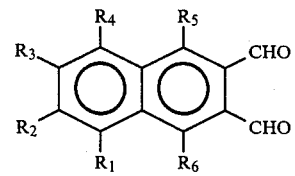

wherein (A) R$_1$ is H, N(CH$_3$)$_2$, SO$_3$H, NO$_2$, SO$_3^-$Na$^+$ or

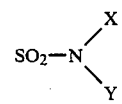

wherein X and Y are identical or different and are hydrogen or alkyl and R$_2$, R$_3$, R$_4$, R$_5$, and R$_6$ are H; or
(B) R$_1$, R$_4$, R$_5$, and R$_6$ are H, and

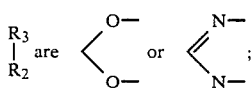

or (C) $R_1$ and $R_4$ are $N(CH_3)_2$ or

and $R_2$, $R_3$, $R_5$, and $R_6$ are H; or (D) $R_1$, $R_2$, $R_3$, and $R_4$ are H and $R_5$ and $R_6$ are $OCH_3$,

$OSi(CH_3)_2$ $C_4H_9$, or $N(CH_3)_2$; or (E) $R_1$, $R_4$, $R_5$, and $R_6$ are H and $R_2$ and $R_3$ are $CH_3O$,

$SO_3H$ or $CO_2H$ or the salts thereof;

(F) $R_1$, $R_3$, $R_4$, $R_5$, and $R_6$ are H and $R_2$ is $(CH_3)_2N$.

4. The method of claim 11 wherein said reagent is a substituted or unsubstituted naphthalene-2,3-dicarboxaldehyde of the formula:

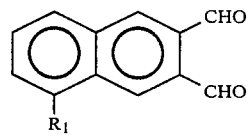

wherein $R_1$ is H, $N(CH_3)_2$, $SO_3H$, $NO_2$, or $SO_3{}^-Na^+$.

5. The method of claim 1 wherein said reagent is unsubstituted naphthalene-2,3-dicarboxaldehyde of the formula:

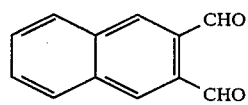

6. The method of claim 1 wherein a plurality of primary amines are reacted with the reagent and cyanide ions.

7. The method of claim 6 further comprising the step of separating said plurality of primary amines into individual amines.

8. The method of claim 7 wherein said separating step is carried out by high performance liquid chromatography.

9. The method of claim 7 wherein said separating step is carried out before said reacting step.

10. The method of claim 7 wherein said separating step is carried out after said reacting step.

11. The method of claim 10 wherein said reagent is a naphthalene-2,3-dicarboxaldehyde that is di-substituted or tetra-substituted.

12. The method of assaying primary amines comprising fluorometrically or electrochemically assaying an adduct formed by reacting a substituted or unsubstituted naphthalene-2,3-dicarboxaldehyde, reactive with primary amines and cyanide, with cyanide and at least one primary amine.

13. A method of assaying primary amines comprising fluorometrically or electrochemically assaying an adduct formed by reacting a substituted or unsubstituted o-phthalaldehyde, reactive with primary amines and cyanide, with cyanide and at least one primary amine.

* * * * *